United States Patent [19]

Knifton et al.

[11] Patent Number: 5,059,725

[45] Date of Patent: Oct. 22, 1991

[54] ONE STEP SYNTHESIS OF METHYL T-BUTYL ETHER FROM T-BUTANOL PLUS METHANOL USING GROUP IV OXIDES TREATED WITH SULFATES OR SULFURIC ACID

[75] Inventors: John F. Knifton, Austin; John R. Sanderson, Leander, both of Tex.

[73] Assignee: Texaco Chemical Company, White Plains, N.Y.

[21] Appl. No.: 677,192

[22] Filed: Mar. 29, 1991

[51] Int. Cl.$^5$ .............................................. C09D 41/00
[52] U.S. Cl. .................................. 568/698; 502/216
[58] Field of Search ......................................... 568/698

[56] References Cited

U.S. PATENT DOCUMENTS 3,920,582 11/1975 Rona .................................... 568/698
4,822,921 4/1989 Knifton et al. ....................... 568/698

FOREIGN PATENT DOCUMENTS 61-17528 1/1986 Japan .................................... 568/698
1373703 8/1986 U.S.S.R. .............................. 568/698

*Primary Examiner*—Howard T. Mars
*Assistant Examiner*—Kimberly J. Kestler
*Attorney, Agent, or Firm*—Jack H. Park; Kenneth R. Priem; Cynthia L. Kendrick

[57] ABSTRACT

Disclosed is a method wherein t-butanol is reacted with methanol in one step to provide methyl t-butyl ether at a temperature of about 20° C. to 250° C. and a pressure of about atmospheric to about 1000 psig employing a catalyst consisting of a Group IV oxide on which there has been deposited a sulfur-containing compound from the group consisting of ammonium sulfate or sulfuric acid.

13 Claims, 1 Drawing Sheet

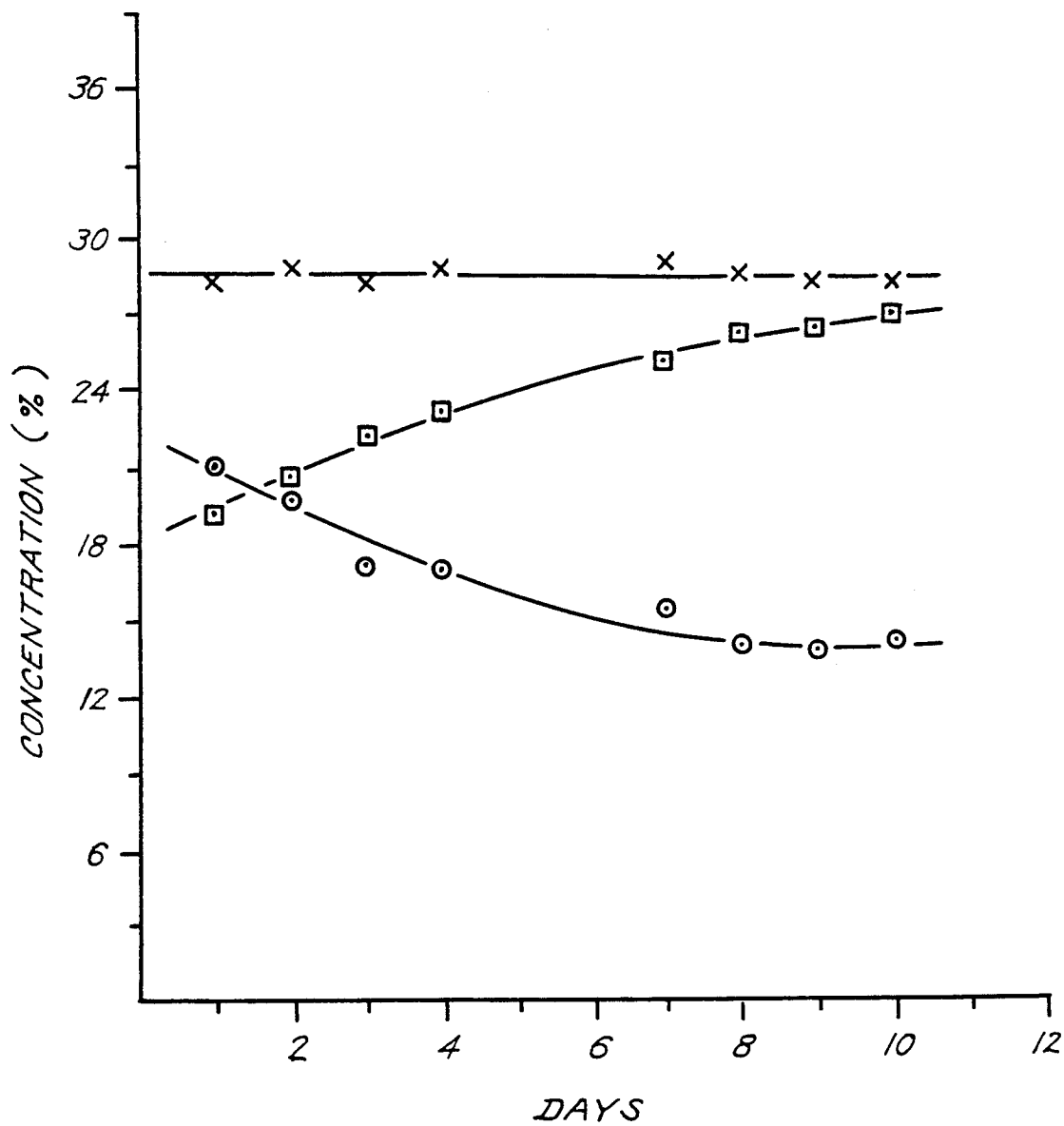

ONE STEP SYNTHESIS OF METHYL T-BUTYL ETHER FROM T-BUTANOL PLUS METHANOL USING GROUP IV OXIDES TREATED WITH SULFATES OR SULFURIC ACID

CROSS-REFERENCE

This application is related to U.S. Pat. Nos. 4,827,048 and 4,822,921 and the copending application Ser. Nos. 07/494,280; 07/494,281 and 07/663,527.

FIELD OF THE INVENTION

This invention concerns an improved process for preparing methyl tertiary butyl ether (MTBE) by the reaction of tertiary butanol and methanol in the presence of a catalyst comprising a Group IV oxide treated with ammonium sulfate or sulfuric acid. Good performance was demonstrated for an extended period and total MTBE plus isobutylene selectivity remains close to quantitative. Where the levels of t-butanol conversion are high, typically >80%, phase separation of the crude product into an isobutylene-MTBE rich phase and a heavier aqueous methanol phase may be observed.

BACKGROUND OF THE INVENTION

It is known to those skilled in the art that ethers, including unsymmetrical ethers, may be prepared by reacting an alcohol with another alcohol to form the desired product. The reaction mixture, containing catalyst and/or condensing agent may be separated and further treated to permit attainment of the desired product. Such further treatment commonly includes one or more distillation operations.

Methyl tert-butyl ether is finding increasing use as a blending component in high octane gasoline as gasoline additives based on lead and manganese have been phased out. Currently all commercial processes for the manufacture of methyl tert-butyl ether are based upon the liquid-phase reaction of isobutylene and methanol (Eq. 1), catalyzed by a cationic ion-exchange resin (see, for example: Hydrocarbon Processing, Oct. 1984, p. 63; Oil and Gas J., Jan. 1, 1979, p. 76; Chem. Economics Handbook-SRI, Sept. 1986, p. 543–7051P). The cationic ion-exchange resins used in MTBE synthesis normally have the sulfonic acid functionality (see: J. Tejero, J. Mol. Catal., 42 (1987) 257; C. Subramamam et al., Can. J. Chem. Eng., 65 (1987) 613).

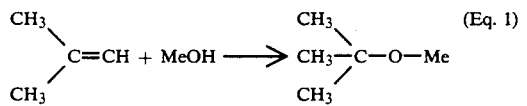

With the expanding use of MTBE as an acceptable gasoline additive, however, a growing problem is the availability of raw materials. Historically, the critical raw material is isobutylene (Oil and Gas J., June 8, 1987, p. 55). It would be advantageous, therefore, to have a process to make MTBE that does not require isobutylene as a building block. It would be advantageous to have an efficient process for making MTBE by reaction of methanol with tertiary butyl alcohol, since t-butanol (TBA) is readily available commercially through isobutane oxidation.

In U.S. Pat. No. 4,144,138 (1979) to Rao et al., there is disclosed a method for recovering methyl tertiary butyl ether from etherification reaction effluent by azeotropic distillation to recover methanol-ether azeotrope overhead which is water-washed to give pure ether raffinate, the latter being azeotropically distilled to yield ether-methanol overhead which is recycled to water washing.

The preparation of methyl tert-butyl ether from methyl and tert-butyl alcohols is discussed in S. V. Rozhkov et al., Prevrashch Uglevodorodov, Kislotno-Osnovn. Geterogennykh Katal. Tezisy Dokl. Vses Konf., 1977, 150 (C. A. 92:58165y). Here the TBA and methanol undergo etherification over KU-2 strongly acidic sulfopolystyrene cation-exchangers under mild conditions. This reference contains data on basic parameters of such a process. It is also pointed out that, although a plant for etherification over cation exchangers does not present any problems, considerations include the fact that recycling large amounts of tert-butyl alcohol and methanol, as well as isobutylene, causes the scheme to be somewhat more expensive. Also, the progress of the reaction over cation exchangers is usually complicated by various adsorption and diffusion factors, by swelling phenomena, and by the variable distribution of the components between the solution and ion-exchanger phase. Furthermore, said acidic cation-exchangers with an organic (polystyrene or polymethacrylate) backbone generally have a very limited stability range with regard to operating temperatures, with temperatures above 120° C. normally leading to irreversible destruction of the resin and loss of catalytic activity.

In U.S. Pat. No. 2,282,469 to Frolich there is disclosed a process for preparing methyl tertiary butyl ether over a catalyst comprising Kieselguhr impregnated with phosphoric acid at a temperature of about 175° F. to 350° F.

Japanese Patent 0007432 teaches the use of zeolites to make dialkyl ethers containing primary or secondary alkyl groups. The zeolites have a porous structure and are represented by:

$$M_{2/n}O.Al_2O_3.xSiO_2.yH_2O$$

where M is an alkali metal or alkaline earth metal cation or organic base cation, n is the valence of the cation and x and y are variables.

U.S. Pat. No. 4,058,576 to Chang et al. teaches the use of (pentasil-type) aluminosilicate zeolites, such as ZSM-5, having a pore size greater than 5 angstrom units and a silica-to-alumina ratio of at least 12, to convert lower alcohols to a mixture of ethers and olefins.

In an article titled "Design of Sulfur-Promoted Solid Superacid Catalyst" by K. Tanabe and T. Yamaguchi in Successful Design of Catalyst, Inui, T. (Editor) Elsevier Science Publishers B. V. Amsterdam, 1988, p. 99, there is a discussion of the extremely high catalytic activities of sulfur-promoted superacids, including the factors controlling super acidity. Solid superacids such as $SO_4^{2-}/ZrO_2$, $SO_4^{2-}/TiO_2$ and $SO_4^{2-}/Fe_2O_3$ have been reported to exhibit extremely high catalytic activities for acylation and alkylation of aromatics, esterification of phthalic acid, skeletal isomerization of paraffins, dehydration of alcohols, polymerization of alkyl vinyl ethers, liquefaction of coal and rearrangement of oximes.

It is noted that the strength of the superacid depends on the extent of losing the S=O double bond character by an electronic shift from an adsorbed basic molecule to the sulfur complex. The larger the shift, the higher the acid strength.

The acid strength can vary depending on the preparation method, however, the acid strength of $SO_4^{2-}/ZrO_2$ is apparently 10,000 times higher than that of 100% $H_2SO_4$. The effect of the addition of $SO_4^{2-}$ on catalytic activity is surprisingly large.

Ibid., page 101, there is a comparison of the acidities achieved by introduction of various sulfur compounds, such as ammonium sulfate, $SO_3$, $SO_2$, or $H_2S$, onto $ZrO_2$, $TiO_2$, $Fe_2O_3$, $Al_2O_3$, $SnO_2$, $SiO_2$ and $Bi_2O_3$. From a comparison of experimentally obtained spectra of sulfur-promoted oxides under various conditions, it was observed that whatever the starting sulfur compounds are, once they were oxidized on the surface of $ZrO_2$, $TiO_2$ and $Fe_2O_3$, they form a structure in which the presence of two covalent SO double bonds is characteristic. The structure is responsible for the generation of the strong acidity and a central metal cation plays as a Lewis acid site. The formation is basically a chemical reaction between $SO_4^{2-}$, $SO_2$ or $SO_3$ and the oxide surfaces to form the definite structure in which two covalent bonds are involved.

Results indicated that when a basic molecule is adsorbed on the central metal cation, it tends to reduce the bond order of SO from a highly covalent double-bond character to a lesser double-bond character.

The stability of the catalyst upon hydrogen reduction at various temperatures, and the facility of regeneration upon reoxidation was tested using the dehydration of 2-propanol as the test reaction. The catalytic activity decreased with increase in reduction temperature from 100° to 450° C. It was theorized that the activity loss by reduction at lower temperatures might be the result of the removal of surface oxygens since recovery of the catalysts by oxidation was possible to varying extents.

It was observed that only $ZrO_2$, $TiO_2$ and $Fe_2O_3$ gave strong acidity by sulfur promotion, possibly because the number of acid sites thus obtained may be limited by the surface area of the oxides.

Superacid catalysts are particularly desirable for reactions where lower temperatures are favored.

In an article by O. Saur et al., J. Catal., 99, (1986) titled "The Structure and Stability of Sulfated Alumina and Titania," sulfated alumina and titania were studied using infrared spectroscopy and a vacuum microbalance with the aim of determining the structure of the surface sulfate, its thermal stability, and its reducibility in $H_2$. It was concluded that the sulfated $TiO_2$ or $Al_2O_3$ has a structure resembling ($M_3O_3$)S=O[M=Al or Ti], whereas in the presence of $H_2O$ or excess surface OH groups, this is converted to

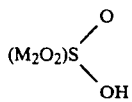

type groups, thus accounting for the increased Bronsted activity. Finally, the sulfated $Al_2O_3$ surface was found to be both more thermally stable and more resistant to reduction in $H_2$ than the sulfated $TiO_2$ and the authors state, "sulfates of titania are known to be relatively unstable."

There is a discussion titled "Dehydration of Alcohols Catalyzed by Metallic Sulphates Supported on Silica Gel," in J. Chem. Soc. Perkin Trans. I, 1989, 707, authored by T. Nishiguchi and C. Kamio. In this work metallic sulphates and hydrogen sulphates supported on silica gel efficiently catalyzed dehydration of secondary and tertiary alcohols under mild conditions. The dehydration catalytic activity of the sulphates and hydrogen sulphates was examined in the case of cyclododecanol. The sulphates of Ce, Ti and Fe were most active. Silica gel was essential for the efficient dehydration in each case.

Ammonium sulfate was not referred to and the indication was that this type catalyst was unsuitable for primary alcohols. On page 709, Col. 1, lines 3-5, it is stated that primary alcohols failed to react.

The authors suggest that the greater the Lewis acidity of a sulphate, the greater its activity on silica gel and, further, that the proton liberated from hydrogen sulphates presumably contributes to the high activity of the salts because the salts of Na, K and $NH_4$ on silica gel were inactive.

In Catalysis Today, 5 (1989) 493-502 there is an article titled "n-Butane Isomerization on Solid Superacids," by J. C. Yori et al., in which the use of $ZrO_2/SO_4^{2-}$ to isomerize n-butane and method of preparation of $ZrO_2/SO_4^{2-}$ is discussed. The $ZrO_2/SO_4^{2-}$ was calcinated at between 773° K. and 933° K. and optimum catalytic activity was found where calcination took place around 893° K.

Ishida et al. report in Chem. Lett., 1869, 1988 on the "Acid Property of Sulfur-Promoted Zirconium Oxide on Silica as Solid Superacid." Here it was concluded that the higher acid strength of the catalyst can best be achieved after the crystal growth of the supported oxide, and that a tetragonal form of $ZrO_2$ grows extensively when the amount of $ZrO_2$ loaded becomes large. This relationship between crystal growth and generation of acidity may be of significance in designing a catalyst having a higher number of acid sites.

Recently in Bull. Chem. Soc. Jpn., 63, (1990), 244-246 K., Arata et al. found that where the acidity and catalytic activity of $Zr(SO_4)_2$ and $Ti(SO_4)_2$ calcined at 500°-800° C. were studied, the products obtained by calcination at 725° C. for $Zr(SO_4)_2$ and at 625° C. for $Ti(SO_4)_2$ showed the highest activity for the cracking of cumene compared with samples calcined at other temperatures. The $Zr(SO_4)_2$ was used to crack cumene and also pentane.

More recently, in an article titled "Recent Progress in Solid Superacid," in Applied Catalysis, 61 (1990) 1-25, T. Yamaguchi reviews literature on solid superacids including a discussion of mounted acids, combined acids, and sulfate-promoted metal oxides. It is noted at page 13 that sulfate-promoted metal oxides are useful as catalysts for skeletal isomerization of paraffins, polymerization of ethers, acetylation, benzolation and esterification.

At page 23 of this article it is stated that "$SO_4^{2-}$ promoted $ZrO_2$ and $Fe_2O_3$ can catalyse the skeletal isomerization of alkanes, but the catalyst life was not sufficient for industrial use."

At page 24 the authors project a number of processes in which solid superacids might be useful. The reaction of primary and tertiary alcohols over such a catalyst is not mentioned or suggested.

There is a need in the art for a stable catalyst for producing MTBE. It would be especially desirable if the catalyst allowed the reaction to be accomplished in one step under relatively mild conditions, but was thermally and chemically stable at higher temperatures. Although some of the work discussed above suggests the isomerization of alkanes or dehydration of alcohols, there seems to be nothing in the art which suggests that reacting a primary and tertiary alcohol such as methanol and t-butanol over a solid superacid would produce MTBE and isobutylene. Further the related art would seem to indicate catalysts such as $TiO_2/SO_4$ would be poor candidates for industrial use. It has now been discovered that a catalyst composition comprising sulfuric acid on a Group IV metal oxide or a Group IV oxide having ammonium sulfate calcinated thereon provides these desirable characteristics and good yields of a valuable product. The catalysts have performed well over a 10-day period in the manufacture of MTBE. They exhibit good stability and show promise for suitability for commercial use which the art suggests is unfeasible.

SUMMARY OF THE INVENTION

In accordance with certain of its aspects, the novel method of this invention for preparing ethers from primary alcohols and tertiary alcohols, and especially methyl tert-butyl ether from tertiary butyl alcohol (t-butanol) and methanol in one-step, comprises reacting tertiary butyl alcohol and methanol in the presence of a catalyst comprising a Group IV oxide treated with a sulfur compound, from the group consisting of sulfuric acid or a sulfate compound, at an elevated temperature and moderate pressure. Examples demonstrate the particular effectiveness of sulfated zirconia or titania which has been calcined at 625° C. or higher and sulfuric acid on titania.

DETAILED DESCRIPTION OF THE DRAWING

FIG. 1 represents the concentration of isobutylene, methyl tertiary butyl ether and t-butanol over a period of days where the catalyst is sulfuric acid-on-zirconia.

DESCRIPTION OF THE INVENTION

Preparation of the product of this invention may be carried out typically by the etherification in one step of tertiary and primary alcohols in the presence of a catalyst which preferably comprises a Group IV oxide having ammonium sulfate deposited thereon or sulfuric acid on a Group IV oxide.

The reaction can be represented by the following:

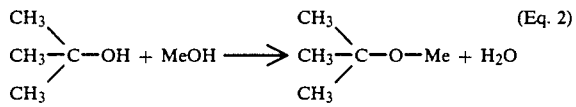
(Eq. 2)

The reactants comprise mixtures of primary alcohols and tertiary alcohols which can be reacted over the catalyst to produce alkyl tertiary alkyl ethers. For example, methanol and t-butanol (tBA) coreactants are reacted to form MTBE and may be mixed in any proportion in order to generate the desired methyl t-butyl ether, but preferably the molar ratio of methanol to t-butanol in the feed mixture should be between 10:1 and 1:10, if the yield of desired MTBE is to be maximized. In order to achieve maximum selectivity to MTBE, and optimum conversion per pass, an excess of methanol in the liquid feed is desirable. The most preferred methanol-to-tertiary butanol molar ratio is from 1:1 to 5:1.

In certain circumstances, it may be particularly desirable that the t-butanol conversion be high enough (e.g. >80% per pass), such that the crude product mix phase separates into an isobutylene-MTBE product-rich phase and a heavier aqueous methanol phase. Preferably such a product phase separation would be achieved at as low an etherification temperature as possible, but particularly in the range 160°-200° C.

The same process may also be applied to the preparation of other alkyl tertiary alkyl ethers, such as, for example ethyl t-butyl ether (ETBE), TAME, etc. Said process may be applied to the reaction of a $C_1-C_6$ primary alcohol such as methanol, ethanol, n-propanol and n-hexanol with a $C_4-C_{10}$ tertiary alcohol such as, for example, tertiary butanol and tertiary amyl alcohol. Reaction of methanol with tertiary amyl alcohol (2-methyl-2-butanol) would then yield methyl tertiary amyl ether (TAME). Alternatively a mixture of alcohols, e.g., a mixture of $C_1-C_5$ alcohols, could be reacted to give a mixture of alkyl tert-alkyl ethers.

The catalyst of this invention consists of Group IV oxides treated with certain sulfur-containing compounds. In the primary embodiment, Group IV oxides are sulfated by treatment with a sulfate-containing compound.

The Group IV oxides can be sulfated by the use of ammonium sulfate, ammonium hydrogen sulfate, or sulfuric acid as the sulfur-containing compound, as well as sulfur trioxide, sulfur dioxide and hydrogen sulfide. The preferred sulfating agents are ammonium sulfate and sulfuric acid. Said agents may be employed neat, or as an aqueous, ketonic, alcoholic, or ether solution, but preferably as an aqueous solution. Said sulfating agents may also be employed as mixtures thereof. Excess sulfating agent may be removed by a number of procedures including filtration and evaporation.

The preformed, sulfated Group IV oxide may then, optionally, be calcined prior to use as an etherification catalyst. Calcination in air or in an inert gas environment, such as nitrogen, may be conducted at a temperature of at least 100° C., but below the temperature at which thermal destruction leads to catalyst deactivation. This can be determined by routine experimentation for a particular catalyst. The sulfated catalyst is typically calcined for from 1 to 24 hours at a temperature of from about 500° to 800° C. Good results were achieved, for example, for the ammonium sulfate on zirconia catalyst by calcining at 625°-750° C., for 16-20 hours, in a stream of nitrogen. Temperatures above 900° C. should be avoided.

Suitable Group IV oxides used in conjunction with said sulfur-containing compounds include the oxides of aluminum, silicon, titanium, zirconium, hafnium, germanium, tin and lead, as well as combinations thereof. Particularly preferred are oxides of titanium and zirconium, such as the anatase or rutile forms of titania, or zirconia.

In a more specific embodiment, the Group IV oxide is treated with sulfuric acid by adding said acid neat, or diluted with distilled water, to the oxide extrudates, mixing for 1 to 24 hours, filtering, washing and calcining in a stream of air for about 1 to 24 hours. The prepared sulfuric acid-treated oxide should then have a titratable acidity of at least 0.1 meq/g.

The weight percent of sulfuric acid to Group IV support should be such that the concentration of the sulfur in the formulated catalyst is in the range of 0.1 wt % to 30 wt %, although concentrations outside this range may also be employed. Where sulfuric acid, for example, is supported on titania, a suitable quantity of sulfur is >0.5 wt %.

Generally, the catalyst composition is prepared by impregnating a preformed pellet. A suitable procedure to be used is to immerse titania pellets, for example, in an aqueous or polar organic solvent (such as acetone) solution of the acid, preferably at ambient temperature. Higher temperatures of about 100° to about 150° C. can be used, if desired. This treatment should be continued, preferably with agitation, for about 0.1 to about 5 hours sufficient to permit the solution to penetrate the pores of the titania pellet. Suitably, the amount of solution of the acid that is used should be adequate to permit full immersion of the titania pellets. Larger amounts of the solution can be used, if desired, but there is no particular advantage in doing so. At the end of the immersion step, the excess solution can be evaporated from the treated pellets, or the pellets can be removed from the solution and permitted to dry (e.g., in a drying oven).

The Group IV oxide may be in the form of powders, pellets, spheres, shapes and extrudates. The examples described herein demonstrate the advantages of using pellets and extrudates. Titania pellets can be prepared by extrusion or by compaction in conventional pelleting apparatus using a pelleting aid such as graphite. Extrudates which work well include HSA titania carrier extrudate from Norton Company, with a surface area of 51 m²/g, and zirconia extrudates from Norton having a surface area of 77 m²/g.

As will be demonstrated by the examples, the Group IV oxides are preferably of high purity and high surface area. It has been found in the process of this invention that greater conversion of tertiary butanol and methanol is achieved where the surface area of the support is generally >10 m²/g.

Cylindrically-shaped catalyst pellets having a diameter essentially equal to the length thereof can be employed. Diameters ranging from about 0.794 mm (1/32 inch) to about 9.525 mm (⅜ inch) possess desirable dimensions. It will be understood that the shape and dimensions of the pellets are not critical to the present invention and that pellets of any suitable shape and dimensions may be used as desired by one wishing to practice the process of the present invention.

When cylindrical pellets of catalyst of the type described above are used, the liquid hourly space velocity may be varied within wide limits (e.g., 0.1 to 10) in order to obtain a desired rate of conversion, as explained above. Normally, space velocities of about 0.5 to 2 LHSV will be employed.

The pelleted catalyst compositions of the present invention are preferably employed as a fixed bed of catalyst in a continuous reaction system. In a continuous process of this nature, the time of contact of the reactants with the catalyst is one of the interrelated factors that those skilled in the art will adjust, along with temperature, pressure, bed geometry, pellet size, etc. in order to obtain a desired rate of reaction and, hence, a desired percentage of conversion of the reactants. Thus, in a continuous process, it is not necessary to drive the reaction to completion because unreacted feedstock components can be recycled to the reactor.

Catalyst life is an important factor in conducting a continuous reaction. For example, if a catalyst is easily poisoned, or if catalyst pellets do not have good structural properties, the economics of the process will be adversely affected. The catalysts of the present invention are relatively insensitive to poisoning, so this should not present a problem.

As a consequence, the catalyst compositions of the present invention are advantageously used in a continuous process for the continuous production of methyl t-butyl ether reaction products from tertiary butanol and methanol. Such catalyst compositions can be used for prolonged periods without the need for regeneration. Nevertheless, with the passage of time deactivation will tend to slowly occur. Deactivation can be measured qualitatively by the loss of butanol conversion, or as the increase of temperature required to maintain an essentially constant conversion rate for the t-butanol and methanol.

The fact that this method can be achieved under relatively mild operating conditions is an attractive feature of this invention. Etherification can generally be conducted at temperatures from 20° to 250° C. The preferred range is 100° to 200° C. The total operating pressure may be from 0 to 1000 psig, or higher. The preferred pressure range is 50 to 500 psig.

Typically, MTBE is generated continuously in up to ca. 40 wt % concentration in the crude liquid product at total liquid hourly space velocities (LHSV) of at least 0.1 and up to ten, and relatively mild conditions, where:

$$LHSV = \frac{\text{Volume Of Total Liquid Feed Run Through The Reactor Per Hour}}{\text{Volume of Catalyst In Reactor}}$$

The examples which follow illustrate the one-step synthesis of MTBE from TBA and MeOH (Eq. 2) using sulfuric acid-treated and sulfated Group IV oxide extrudates. The examples are only intended as a means of illustration and it is understood the invention is not meant to be limited thereby.

Conversion of t-butanol (TBA, wt %) is estimated in the following examples using the equation:

$$\frac{(\text{Wt \% Conc. of TBA in Feed} - \text{Wt \% Conc. of TBA in Product})}{\text{Wt \% Conc of TBA in Feed}} \times 100$$

Selectivities to methyl t-butyl ether (MTBE, mole %) are estimated from:

$$\frac{\text{Moles of MTBE in Product Liquid}}{\text{Moles of TBA Converted}} \times 100$$

EXAMPLE I

Examples 1 through 6 demonstrate the first embodiment employing ammonium sulfate treated Group IV oxides. It may be noted that:

a) In Example 4, the ammonium sulfate treated zirconium extrudates, after calcination at 625° C., gave MTBE in up to ca. 38% concentration when run at LHSV of 2 using a MeOH/tBA molar feed ratio of 1:1:1. Under these conditions the tBA conversion is typically 71% at 160° C. and 80% at 180° C., while the isobutylene and MTBE molar selectivities are 51 and 46% respectively at 160° C. (Sample #7).

b) MTBE/isobutylene cogeneration has also been demonstrated with an ammonium sulfate-treated titania catalyst, calcined at 625° C., and with an ammonium sulfate-treated zirconia catalyst, calcined at 750° C. (see Examples 5 and 6).

c) In Example 6, using the ammonium sulfate-treated zirconia catalyst, tBA conversion at 160° C. is typically 70%, while the isobutylene and MTBE molar selectivities are 55% and 46% respectively (Sample #5). At 180° C., tBA conversion is >80% and product phase separation into an isobutylene-MTBE product-rich phase and a heavier aqueous methanol-rich phase is observed.

d) Essentially no MTBE formation is detected with the zirconia extrudates that have not been $(NH_4)SO_4$ treated and calcined (see Comparative Example A).

Examples 7 through 13 demonstrate the embodiment using sulfuric acid-treated Group IV oxides. It may be noted that:

a) In Example 8, a sulfuric acid-treated extrudate catalyst performed very well under the fairly forcing conditions used in this test, i.e.: At high operating temperature —160° C. Low methanol to t-butanol molar feed Ratio of 1:1:1. High throughput—LHSV=2.

Tert-butanol conversion levels remained satisfactory at 61% to 71% throughout the test using a fixed-bed, plug-flow, reactor design. While MTBE selectivity increases modestly over this 10 day period, MTBE plus isobutylene remain the major products and in fact $MTBE+C_4H_8$ selectivity is close to quantitative over the life of the run.

b) In Examples 11-13 three catalysts, namely sulfuric acid-on-zirconia, sulfuric acid-on-titania and sulfuric acid-on-silica, are demonstrated to be effective catalysts for MTBE production from tBA plus methanol over a range of operating temperatures (80°-180° C). At 160° C., the order of activity in terms of tBA conversion per pass at LHSV 2 is found to be:

$$H_2SO_4/TiO_2 > H_2SO_4/ZrO_2 >> H_2SO_4/SiO_2$$

c) In Example 12, product phase separation into an isobutylene-MTBE product-rich phase and a heavier aqueous methanol phase is evident at 180° C. tBA conversion is >80%.

EXAMPLE 1

This example illustrated the preparation of a typical ammonium sulfate-treated zirconia catalyst.

Zirconia, high purity, extrudates (200 g, ⅛" diameter, 77 m²/g surface area, from the Norton Company) were covered with about 250 g of an aqueous, 10% solution of ammonium sulfate and the mixture let stand for about 5 minutes. The mixture was then placed in an oven and heated to 625° C. under a nitrogen flow. The oven was held at 625° C. for 20 hours and then cooled to ambient temperature under nitrogen. The formed catalyst was found to have a titratable acidity of 0.21 meq/g and a sulfate content of 2.9%.

EXAMPLE 2

This example illustrated the preparation of a typical ammonium sulfate-treated titania catalyst.

Employing the procedures of Example 1, a sample of titania extrudates (200 g, ⅛" E, 51 m²/g surface area from Norton Company) was treated with aqueous $(NH_4)_2SO_4$ and calcined at 625° C. under nitrogen.

The formed catalyst was found to have a titratable acidity of 0.07 meq/g and a sulfate content of 0.5%.

EXAMPLE 3

Employing the procedures of Example 1, a sample of ammonium sulfate-treated zirconia was prepared where said extrudates were calcined at 750° C. for 16 hours.

EXAMPLE 4

This example illustrates the production of methyl t-butyl ether from t-butanol and methanol using the ammonium sulfate-treated zirconia catalyst of Example 1.

Synthesis was conducted in a tubular reactor (½" id., 12" long), constructed of 316 stainless steel, operated upflow, and mounted in a furnace controllable to ±1.020 C. and fitted with pumps allowing flow control to ±1 cc/hr. The reactor was also fitted with a pressure regulating device and equipment for monitoring temperature, pressure and flow rate.

The reactor was charged at the beginning of the experiment with 25 cc of ammonium sulfate-treated zirconia prepared by the method of Example 1. A screen of glass wool was placed at the top and bottom of the reactor to ensure the catalyst would remain in the middle portion.

The catalyst bed was treated with methanol/t-butanol (1.1:1 molar mix) upflow, at a flow rate of 50 cc/hr., while the reactor was held at 100° C., with a total pressure of 300 psi. Samples of crude product effluent were collected periodically on stream, in 316 ss bombs, and analyzed by glc and gc-ir.

Typical analyses data for samples taken under these conditions are summarized in Table I. Performance at a series of other temperatures (120°, 140°, 160° and 180° C.) and flow rates (200 cc/hr.) was measured using the same procedures. These results are also given in Table I. Of note, the conversion levels and isobutylene/MTBE selectivities at 160° and 180° C. are as follows:

| SAMPLE | OPERATING TEMP(°C.) | tBA CONC.(%) | MOLAR SELECTIVITY (%) | |
|--------|---------------------|--------------|-------|------|
|        |                     |              | $C_4H_8$ | MTBE |
| 7      | 160                 | 71           | 51    | 46   |
| 10     | 180                 | 80           | 74    | 31   |

The high overall isobutylene plus MTBE selectivity at 180 20 C. operating temperature indicates the onset of phase separation in the crude product effluent.

EXAMPLES 5-6

These examples illustrate the production of methyl t-butyl ether from t-butanol and methanol using the ammonium sulfate-treated Group IV oxide catalysts of Examples 2 and 3.

Synthesis procedures and operating conditions were as described in Example 4, the results are tabulated in Tables II and III.

For Example 6, Sample 5, taken at 160° C., it may be noted that:
t-Butanol conversion is 70%
isobutylene selectivity is 55 mole %
MTBE selectivity is 46 mole %

COMPARATIVE EXAMPLE A

This example illustrates that methyl t-butyl ether is not generated from t-butanol and methanol when the catalyst is a Group IV oxide alone, e.g. zirconia extrudates (⅛" diameter).

Synthesis procedures and operating conditions were as described in Example 4. The results are tabulated in Table IV.

TABLE I

MTBE FROM MeOH/tBA

| Ex. | Catalyst | MeOH/tBA Molar Ratio | Temp. (°C.) | Feed Rate (cc/hr) | Time on Stream (Days) | SAMPLE | H₂O | MeOH | C₄H₈ | tBA | MTBE |
|---|---|---|---|---|---|---|---|---|---|---|---|
| 4 | Example 1[a] | 1.1:1 | | | | FS-1 | | 31.5 | | 68.4 | |
| | | | 100 | 50 | 1 | 1 | 3.1 | 26.9 | 2.7 | 53.6 | 13.6 |
| | | | | | | 2 | 3.2 | 26.9 | 2.7 | 54.2 | 12.9 |
| | | | 120 | 50 | 2 | 3 | 6.4 | 24.3 | 5.1 | 42.7 | 21.3 |
| | | | | | | | 7.0 | 23.6 | 5.6 | 41.0 | 22.7 |
| | | | 140 | 50 | 3 | 5 | 12.0 | 18.5 | 10.1 | 26.2 | 33.1 |
| | | | | | | 6 | 12.3 | 18.4 | 10.3 | 26.0 | 32.7 |
| | | | 160 | 50 | 4→ | 7 | 13.8 | 20.7 | 18.8 | 20.0 | 26.6 |
| | | | | | | 8 | 13.8 | 20.9 | 18.4 | 20.7 | 26.1 |
| | | | 180 | 50 | | 9 | 10.6 | 21.5 | 18.2 | 11.4 | 38.0 |
| | | | | | 5→ | 10 | 7.3 | 21.6 | 30.7 | 13.5 | 26.6 |
| | | | 160 | 200 | 6 | 11 | 3.4 | 27.2 | 4.4 | 52.9 | 12.1 |
| | | | | | | 12 | 3.5 | 27.5 | 4.4 | 52.5 | 12.1 |

[a]Ammonium sulfate-treated zirconia, Δ 625° C.

TABLE II

MTBE FROM MeOH/tBA

| Ex. | Catalyst | MeOH/tBA Molar Ratio | Temp. (°C.) | Feed Rate (cc/hr) | Time on Stream (Days) | SAMPLE | H₂O | MeOH | C₄H₈ | tBA | MTBE |
|---|---|---|---|---|---|---|---|---|---|---|---|
| 5 | Example 2[a] | 1.1:1 | | | | FS-1 | | 31.5 | | 68.2 | |
| | | | 120 | 50 | 1 | 1 | 1.2 | 30.3 | 2.0 | 61.7 | 4.6 |
| | | | | | | 2 | 1.0 | 30.1 | 1.8 | 62.3 | 4.5 |
| | | | 140 | 50 | 2 | 3 | 2.4 | 28.8 | 3.8 | 56.5 | 8.3 |
| | | | | | | 4 | 2.3 | 29.3 | 3.4 | 57.7 | 7.1 |
| | | | 160 | 50 | 3 | 5 | 2.5 | 28.8 | 4.2 | 56.5 | 7.8 |
| | | | | | | 6 | 2.6 | 28.5 | 4.9 | 55.4 | 8.4 |
| | | | 180 | 50 | 4 | 7 | 9.8 | 25.1 | 17.4 | 30.4 | 17.1 |
| | | | | | | 8 | 9.3 | 25.5 | 17.0 | 31.4 | 16.6 |

[a]Ammonium sulfate-treated titania, Δ 625° C.

TABLE III

MTBE FROM MeOH/tBA

| Ex. | Catalyst | MeOH/tBA Molar Ratio | Temp. (°C.) | Feed Rate (cc/hr) | Time on Stream (Days) | SAMPLE | H₂O | MeOH | C₄H₈ | tBA | MTBE |
|---|---|---|---|---|---|---|---|---|---|---|---|
| 6 | Example 3[a] | 1/1:1 | | | | FS-1 | | 31.7 | | 68.2 | |
| | | | 120 | 50 | 1 | 1 | 9.9 | 20.3 | 7.3 | 33.8 | 28.5 |
| | | | | | | 2 | 7.1 | 23.4 | 6.2 | 40.0 | 23.0 |
| | | | 140 | 50 | 2 | 3 | 10.8 | 19.6 | 11.0 | 26.0 | 32.3 |
| | | | | | | 4 | 10.9 | 19.7 | 11.0 | 26.0 | 32.2 |
| | | | 160 | 50 | 3 | 5→ | 12.0 | 21.4 | 20.0 | 20.3 | 26.1 |
| | | | | | | 6 | 13.0 | 21.6 | 21.8 | 17.5 | 25.9 |
| | | | 180 | 50 | 4 | 7 | 2.2 | 10.4 | 56.7 | 5.4 | 24.7 |
| | | | | | | | 31.4 | 43.0 | 9.8 | 7.5 | 8.0 |
| | | | | | | 8 | 1.5 | 9.0 | 62.3 | 4.4 | 22.6 |
| | | | | | | | 34.5 | 44.9 | 6.3 | 7.1 | 7.0 |
| | | | 160 | 200 | 5 | 9 | | 31.1 | 0.8 | 67.6 | 0.2 |
| | | | | | | 10 | | 31.2 | 0.7 | 67.6 | 0.2 |

[a]Ammonium sulfate-treated zirconia, Δ 750° C.

TABLE IV

MTBE FROM MeOH/tBA

| Ex. | Catalyst | MeOH/tBA Molar Ratio | Temp. (°C.) | Feed Rate (cc/hr) | Time on Stream (Days) | SAMPLE | H₂O | MeOH | C₄H₈ | tBA | MTBE |
|---|---|---|---|---|---|---|---|---|---|---|---|
| A | ZrO₂[a] | 1.1:1 | | | | FS-1 | | 31.5 | | 68.2 | |
| | | | 120 | 50 | 1 | 1 | | 31.6 | 0.6 | 67.6 | |
| | | | | | | 2 | | 31.4 | 0.6 | 67.8 | |

TABLE IV-continued

MTBE FROM MeOH/tBA

| Ex. | Catalyst | MeOH/tBA Molar Ratio | Temp. (°C.) | Feed Rate (cc/hr) | Time on Stream (Days) | ←PRODUCT COMPOSITION (WT %)→ | | | | |
|---|---|---|---|---|---|---|---|---|---|---|
| | | | | | | SAMPLE | H₂O | MeOH | C₄H₈ | tBA | MTBE |
| | | | 140 | 50 | 2 | 3 | | 31.3 | 0.6 | 67.9 |
| | | | | | | | | 31.3 | 0.6 | 67.9 |
| | | | 160 | 50 | 3 | 5 | 0.3 | 31.4 | 0.5 | 67.7 |
| | | | | | | 6 | 0.2 | 31.4 | 0.6 | 67.7 |
| | | | 180 | 50 | 4 | 7 | | 31.3 | 0.6 | 68.0 |
| | | | | | | 8 | | 31.5 | 0.7 | 67.7 |

[a]Norton Company, ⅛" extrudates, Sample #8916133.

EXAMPLE 7

The example illustrates the preparation of a sulfuric acid-treated zirconia catalyst.

To a flask containing 250 cc of zirconia ⅛" diameter extrudates (77 m$_2$/g, from the Norton Company) was added a solution of sulfuric acid (96.8%, 400 g) in 1 liter of distilled water. The mixture was stirred for 1-2 hours and the solids filtered then washed with distilled water until the washings were pH neutral. The white extrudates were calcined at 600° C. in a stream of air for 3 hours.

The titratable acid content of the sulfur acid-treated zirconia was determined to be 0.15 meq/g. The percentage sulfate, by ion chromatography, was 0.73%.

EXAMPLE 8

The example illustrates the production of methyl t-butyl ether from t-butanol and methanol using the sulfuric acid-on-zirconia catalyst of Example 7.

Synthesis was conducted in a tubular reactor (½" id, 12" long), constructed of 316 stainless steel, operated upflow and mounted in a furnace controllable to ±1.0° C. and fitted with pumps allowing flow control to <±1 cc/hr. The reactor was also fitted with a pressure regulating device and equipment for monitoring temperature, pressure and flow rate.

The reactor was charged at the beginning of the experiment with 25 cc of sulfuric acid-on-zirconia catalyst prepared by the procedures of Example 7. A screen of glass wool was placed at the top and bottom of the reactor to ensure the catalyst would remain in place.

A feed mix of methanol/t-butanol (1.1:1 molar ratio) was fed upflow at a rate of 50 cc/hr, while the reactor was held at 160° C. using a total pressure of 300 psi. Samples of upflow product effluent were collected periodically on-stream, in 316 ss bombs, and analyzed by glc.

Typical of analyses data for samples taken under these conditions are summarized in Table 5. Concentrations of isobutylene, MTBE and t-butanol in the crude product are plotted in FIG. 1. For Samples 1 and 8 taken after one and 10 days operating time, respectively, the t-butanol conversion levels and MTBE and isobutylene selectivities are as follows:

| | SAMPLE #1 (1 DAY) | SAMPLE #8 (10 DAYS) |
|---|---|---|
| t-Butanol Conversion | 71 | 61 |
| Isobutylene Selectivity (moles %) | 55 | 44 |
| MTBE Selectivity (Moles %) | 47 | 56 |

TABLE V

MTBE FROM MeOH/tBA

| Ex. | Catalyst | MeOH/tBA Molar Ratio | Temp. (°C.) | Feed Rate (cc/hr) | Time on Stream (Days) | ←PRODUCT COMPOSITION (WT %)→ | | | | | |
|---|---|---|---|---|---|---|---|---|---|---|---|
| | | | | | | SAMPLE | H₂O | MeOH | C₄H₈ | tBA | MTBE |
| 8 | Example 7[a] | 1.1:1 | 160 | 50 | | FS | | 30.1 | | 69.6 | |
| | | | | | 1 | 1→ | 10.8 | 20.6 | 21.0 | 19.2 | 28.3 |
| | | | | | 2 | 2 | 10.4 | 20.4 | 19.6 | 20.8 | 28.7 |
| | | | | | 3 | 3 | 11.2 | 20.6 | 17.3 | 22.3 | 28.3 |
| | | | | | 4 | 4 | 10.2 | 20.6 | 17.0 | 23.3 | 28.9 |
| | | | | | 7 | 5 | 9.6 | 20.5 | 15.4 | 25.3 | 29.2 |
| | | | | | 8 | 6 | 9.5 | 20.8 | 14.4 | 26.5 | 28.6 |
| | | | | | 9 | 7 | 10.2 | 20.8 | 13.8 | 26.7 | 28.4 |
| | | | | | 10 | 8→ | 9.6 | 20.9 | 14.1 | 27.0 | 28.4 |

[a]Sulfuric acid treated zirconia, Δ 600° C.

EXAMPLE 9

This example illustrates the preparation of a sulfuric acid-on-titania solid super acid.

To a flask containing 250 cc of titania ⅛" tablets (158 m²/g surface area, from the Calsicat Company) was added 150 cc of 96.8% concentrated sulfuric acid. The mixture was stirred for 1-2 hours and the solids filtered then washed with distilled water until the washings were pH neutral. The grey tablets were dried at 40° C. overnight in vacuo, then at 150° C. for 3 hours.

The titratable acid content of the sulfuric acid-treated titania was determined to be 0.20 meq/g. The percentage sulfate, by ion chromatography, was 1.02%.

EXAMPLE 10

This example illustrates the preparation of a sulfuric acid-on-silica catalyst.

To a flask containing 250 cc of silica 5 mm spheres (130 m²/g surface area, from United Catalyst Company) was added 150 cc of 96.8% concentrated sulfuric acid. The mixture was stirred for 1-2 hours and the solids filtered then washed with distilled water until the washings were pH neutral. The white spheres were dried at 40° C. overnight in vacuo, then at 150° C. for 3 hours. The acid content of the sulfuric acid-treated silica was determined to be 0.19 meq/g. The percentage sulfate, by ion chromatography, was 0.66%.

EXAMPLES 11–13

Following the procedures of Example 8, the production of methyl t-butyl ether from t-butanol plus methanol was demonstrated using three sulfuric acid-on-Group IV metal oxide supported catalysts, namely:

Sulfuric acid-on-zirconia, prepared according to the method of Example 7.

Sulfuric acid-on-titania, prepared according to the method of Example 9.

Sulfuric acid-on-silica, prepared according to the method of Example 10.

In each case, the MTBE synthesis was demonstrated over a range of operating temperatures (typically from 80° to 180° C.) using the same plug reactor design of Example 8.

Typical analyses data for samples taken during the screening of each of these three catalysts are summarized in Tables VI through VIII. At the operating temperatures of 160° C., the t-butanol conversion levels and MTBE and isobutylene selectivities are as follows:

| EXAMPLE CATALYST | 11 $H_2SO_4/ZrO_2$ | 12 $H_2SO_4/TiO_2$ | 13 $H_2SO_4/SiO_2$ |
|---|---|---|---|
| t-Butanol Conv.(%) | 71 | 75 | 36 |
| Isobutylene Sel.(%) | 53 | 57 | 41 |
| MTBE Selectivity (%) | 48 | 42 | 59 |

TABLE VI

MTBE FROM MeOH/tBA

| Ex. | Catalyst | MeOH/tBA Molar Ratio | Temp. (°C.) | Feed Rate (cc/hr) | Time on Stream (Days) | SAMPLE | ←PRODUCT COMPOSITION (WT %)→ | | | | |
|---|---|---|---|---|---|---|---|---|---|---|---|
| | | | | | | | $H_2O$ | MeOH | $C_4H_8$ | tBA | MTBE |
| 11 | Example 7[a] | | | | | FS | | 30.2 | | 69.1 | |
| | | 1.1:1 | 80 | 50 | 2 | 1 | | 28.9 | 1.0 | 66.4 | 3.5 |
| | | | | | | 2 | | 29.0 | 0.9 | 66.0 | 3.5 |
| | | | 100 | 50 | 3 | 3 | 1.8 | 27.2 | 2.4 | 58.3 | 10.4 |
| | | | | | | 4 | 1.6 | 27.0 | 2.4 | 58.4 | 10.5 |
| | | | 120 | 50 | 4 | 5 | 5.1 | 22.7 | 5.5 | 43.2 | 23.4 |
| | | | | | | 6 | 5.6 | 22.8 | 5.3 | 43.7 | 22.6 |
| | | | 140 | 50 | 5 | 7 | 9.5 | 18.4 | 11.0 | 25.5 | 35.4 |
| | | | | | | 8 | 9.8 | 18.5 | 10.7 | 25.9 | 35.0 |
| | | | 160 | 50 | 6 | 9→ | 11.1 | 21.0 | 19.8 | 19.8 | 28.1 |
| | | | | | | 10 | 11.1 | 21.0 | 18.8 | 20.3 | 28.7 |
| | | | 180 | 50 | 7 | 11 | 13.6 | 29.5 | 10.8 | 10.4 | 35.0 |
| | | | | | | | 28.7 | 41.8 | 7.5 | 7.7 | 14.2 |
| | | | | | | 12 | 22.0 | 38.6 | 7.5 | 10.1 | 21.5 |

[a]Sulfuric acid-on-zirconia, Δ 600° C.

TABLE VII

MTBE FROM MeOH/tBA

| Ex. | Catalyst | MeOH/tBA Molar Ratio | Temp. (°C.) | Feed Rate (cc/hr) | Time on Stream (Days) | SAMPLE | ←PRODUCT COMPOSITION (WT %)→ | | | | |
|---|---|---|---|---|---|---|---|---|---|---|---|
| | | | | | | | $H_2O$ | MeOH | $C_4H_8$ | tBA | MTBE |
| 12 | Example 9[a] | | | | | FS | | 30.3 | | 69.3 | |
| | | 1.1:1 | 100 | 50 | 1 | 1 | 1.6 | 28.0 | 2.5 | 59.2 | 8.5 |
| | | | | | | 2 | 1.3 | 27.5 | 2.6 | 59.3 | 9.0 |
| | | | 120 | 50 | 2 | 3 | 6.0 | 23.4 | 6.9 | 41.3 | 22.2 |
| | | | | | | 4 | 5.1 | 23.5 | 6.8 | 42.9 | 21.5 |
| | | | 140 | 50 | 3 | 5 | 10.2 | 18.5 | 13.2 | 22.9 | 35.1 |
| | | | | | | 6 | 10.0 | 18.6 | 13.0 | 23.3 | 35.0 |
| | | | 160 | 50 | 4 | 7 | 13.4 | 22.9 | 22.5 | 16.1 | 25.0 |
| | | | | | | 8→ | 12.3 | 21.9 | 22.7 | 17.0 | 26.0 |
| | | | 180 | 50 | 5 | 9 | 0.8 | 6.6 | 76.1 | 2.0 | 14.3 |
| | | | | | | | 32.5 | 52.8 | 4.9 | 5.1 | 4.3 |
| | | | | | | 10 | 0.7 | 6.7 | 76.0 | 2.1 | 14.4 |
| | | | | | | | 29.8 | 54.8 | 5.6 | 4.8 | 4.6 |

[a]Sulfuric acid-on-titania.

TABLE VIII

MTBE FROM MeOH/tBA

| Ex. | Catalyst | MeOH/tBA Molar Ratio | Temp. (°C.) | Feed Rate (cc/hr) | Time on Stream (Days) | SAMPLE | ←PRODUCT COMPOSITION (WT %)→ | | | | |
|---|---|---|---|---|---|---|---|---|---|---|---|
| | | | | | | | $H_2O$ | MeOH | $C_4H_8$ | tBA | MTBE |
| 13 | Example 10[a] | | | | | FS | | 30.1 | | 69.6 | |
| | | 1.1:1 | 100 | 50 | 1 | 1 | | 29.6 | 1.1 | 66.5 | 2.6 |
| | | | | | | 2 | 0.1 | 29.3 | 1.0 | 66.6 | 2.6 |

TABLE VIII-continued

MTBE FROM MeOH/tBA

| Ex. | Catalyst | MeOH/tBA Molar Ratio | Temp. (°C.) | Feed Rate (cc/hr) | Time on Stream (Days) | SAMPLE | H$_2$O | MeOH | C$_4$H$_8$ | tBA | MTBE |
|---|---|---|---|---|---|---|---|---|---|---|---|
| | | | 120 | 50 | 2 | 3 | 1.0 | 28.6 | 2.3 | 61.6 | 6.4 |
| | | | | | | 4 | 0.8 | 28.2 | 2.1 | 62.7 | 6.1 |
| | | | 140 | 50 | 3 | 5 | 3.1 | 26.1 | 4.9 | 52.4 | 13.3 |
| | | | | | | 6 | 3.0 | 26.5 | 4.6 | 53.3 | 12.4 |
| | | | 160 | 50 | 4 | 7→ | 4.9 | 24.9 | 7.9 | 44.4 | 17.7 |
| | | | | | | 8 | 4.2 | 25.3 | 7.1 | 47.0 | 16.2 |
| | | | 180 | 50 | 5 | 9 | 2.4 | 27.1 | 5.0 | 57.3 | 8.1 |
| | | | | | | | 2.0 | 28.5 | 3.8 | 58.6 | 7.0 |

$^a$Sulfuric acid-on-silica.

COMPARATIVE EXAMPLE A

This example illustrates that methyl t-butyl ether is not generated from t-butanol and methanol when the catalyst is untreated silica.

Synthesis procedures and operating conditions were as described in Example 8. The results are tabulated in Table IX.

TABLE IX

MTBE FROM MeOH/tBA

| Ex. | Catalyst | MeOH/tBA Molar Ratio | Temp. (°C.) | Feed Rate (cc/hr) | Time on Stream (Days) | SAMPLE | H$_2$O | MeOH | C$_4$H$_8$ | tBA | MTBE |
|---|---|---|---|---|---|---|---|---|---|---|---|
| B | Silica KA$^a$ | | | | | | | 30.0 | | 69.6 | |
| | | 1.1:1 | 100 | 50 | 1 | 1 | | 30.5 | | 69.3 | |
| | | | | | | 2 | | 30.2 | 0.5 | 69.1 | |
| | | | 120 | 50 | 2 | 3 | | 30.8 | | 69.0 | |
| | | | | | | 4 | | 30.9 | | 69.0 | |
| | | | 140 | 50 | 3 | 5 | | 30.0 | 0.4 | 69.5 | |
| | | | | | | 6 | | 30.1 | 0.3 | 69.4 | |
| | | | 160 | 50 | 4 | 7 | | 30.0 | 0.6 | 69.3 | |

$^a$United catalyst KA spheres, 5 mm diameter.

What is claimed is:

1. In a method for the synthesis of methyl t-butyl ether from t-butanol and methanol in one step, the improvement comprising accomplishing the reaction in one step, using a catalyst consisting of a Group IV oxide that has been treated with a sulfur-containing compound from the group consisting of ammonium sulfate or sulfuric acid, contacting said t-butanol and methanol in a molar amount of 0.1 to 10 moles of methanol per mole of t-butanol at a temperature of about 20° C. to 250° C. and a pressure of about atmospheric to about 1000 psig and obtaining the MTBE product.

2. The method of claim 1, wherein the Group IV oxide is selected from the group consisting of zirconia, titania and silica.

3. The method of claim 2 wherein the Group IV oxide is zirconia and the sulfur compound is ammonium sulfate.

4. The method of claim 2, wherein the Group IV oxide is titania and the sulfur-containing compound is ammonium sulfate.

5. The method of claim 2, wherein the Group IV oxide is titania and the sulfur-containing compound is sulfuric acid.

6. The method of claim 1 wherein the Group IV oxide is zirconia and the sulfur-containing compound is sulfuric acid.

7. The method of claim 1 wherein the Group IV oxide is silica and the sulfur-containing compound is sulfuric acid.

8. The method of claim 2 wherein the temperature is from about 100° C. to 200° C.

9. The method of claim 2 wherein the catalyst has been calcined at from 500° to 900° C.

10. The method of claim 9 wherein the catalyst has been calcined from 600° C. to 800° C.

11. In a method wherein t-butanol is reacted with methanol to provide methyl t-butyl ether, the improvement comprising accomplishing the reaction in one step using a catalyst consisting of a Group IV oxide from the group consisting of zirconia or titania which has been treated with ammonium sulfate and calcined, contacting said t-butanol and methanol in a molar amount of 0.1 to 10 moles of methanol per mole of t-butanol at a temperature of about 20° C. to 250° C. and a pressure of about atmospheric to about 1000 psig and obtaining the MTBE product.

12. The method of claims 3 or 5 wherein the operating temperature is in the range 160° to 200° C. and the product comprises a two-phase mix of an isobutylene-MTBE product rich phase and a heavier aqueous methanol-rich phase.

13. In a method wherein t-butanol is reacted with methanol to provide methyl t-butyl ether, the improvement of accomplishing the reaction in one step using a catalyst consisting of an oxide of Group IV from the group consisting of zirconia, titania or silica treated with sulfuric acid, contacting said t-butanol and methanol in a molar amount of 0.1 to 10 moles of methanol per mole of t-butanol at a temperature of about 20° C. to 250° C. and a pressure of about atmospheric to about 1000 psig and obtaining the MTBE product.

* * * * *